United States Patent [19]

Laing et al.

[11] 4,284,766

[45] Aug. 18, 1981

[54] PROCESS FOR THE PREPARATION OF CEPHALOSPORIN COMPOUNDS

[75] Inventors: Stuart B. Laing, Harrow; Gordon G. Weingarten, London, both of England

[73] Assignee: Glaxo Group Limited, London, England

[21] Appl. No.: 77,757

[22] Filed: Sep. 20, 1979

[30] Foreign Application Priority Data

Sep. 21, 1978 [GB] United Kingdom ............... 37675/78

[51] Int. Cl.$^3$ ........................................... C07D 501/04
[52] U.S. Cl. ....................................... 544/22; 544/16; 544/21
[58] Field of Search ................................... 544/21, 22

[56] References Cited

U.S. PATENT DOCUMENTS 4,252,974  2/1981  Laing et al. .................... 544/22

OTHER PUBLICATIONS

Weinstock et al., Tet. Letts. (1975), No. 46, 3979–3982.
Rudinskas et al., J. Med. Chem. (1976), vol. 19, No. 12, 1367–1371.
McKenna et al., Tet. Letts. (1977), No. 2, 155–158.

*Primary Examiner*—Paul M. Coughlan, Jr.
*Attorney, Agent, or Firm*—Bacon & Thomas

[57] ABSTRACT

A process for the preparation of cephalosporins having a phosphonocarbamoyloxymethyl group at the 3-position by reacting a cephalosporin having at the 3-position a group

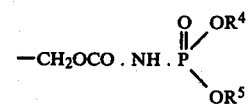

(wherein $R^4$ and $R^5$ are independently alkyl, aralkyl, alicyclic or aryl groups or together form a divalent group) with a compound of formula

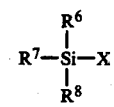

(wherein $R^6$, $R^7$ and $R^8$ are independently alkyl, aralkyl, alicyclic or aryl groups or any two of $R^6$, $R^7$ and $R^8$ together form a divalent group, and X is halogen) followed by hydrolysis. The 3-phosphonocarbamoyloxymethyl cephalosporin products of the process exhibit antibiotic activity, and if desired may be readily converted to 3-carbamoyloxymethyl cephalosporins which themselves show antibiotic activity.

3 Claims, No Drawings

PROCESS FOR THE PREPARATION OF CEPHALOSPORIN COMPOUNDS

This invention is concerned with the preparation of cephalosporin compounds substituted at the 3-position by a phosphonocarbamoyloxymethyl group.

The cephalosporin compounds in this specification are systematically named with reference to "cepham" after *J. Amer. Chem. Soc.,* 1962, 84, 3400; the term "cephem" refers to the basic cepham structure with one double bond.

U.K. Patent Application No. 7,912,215 describes cephalosporin antibiotics which are characterised in that they contain a phosphonocarbamoyloxymethyl (or "dihydroxyphosphorylcarbamoyloxymethyl") group in the 3-position. These cephalosporin compounds show in vivo antibacterial activity against a range of gram-positive and gram-negative organisms. These compounds may also be readily converted to 3-carbamoyloxymethyl cephalosporins which themselves show antibiotic activity.

In particular, U.K. Patent Application No. 7,912,215 discloses 3-phosphonocarbamoyloxymethyl cephalosporin compounds of formula

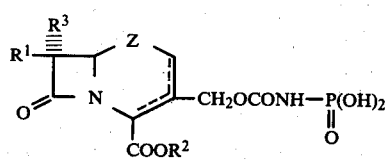

(I)

[wherein $R^1$ represents a protected amino group (e.g. an acylamido group, conveniently one which contains 1–40, e.g. 1–20, carbon atoms, or a precursor therefor); $R^2$ represents hydrogen or a carboxyl blocking group (e.g. the ester-forming residue of an alcohol, phenol, silanol or stannanol, the residue preferably being one which may readily be split off at a later stage); $R^3$ represents hydrogen or a lower (e.g. $C_{1-4}$) alkyl, alkylthio or alkoxy group e.g. a methoxy group; Z is $>S$ or $>S\rightarrow O$ ($\alpha$- or $\beta$-); and the dotted line bridging the 2-, 3- and 4-positions of the molecule indicates that the compounds may be ceph-2-em or ceph-3-em compounds] and salts thereof.

Preferred compounds described in the above-mentioned Application may be represented by the formula

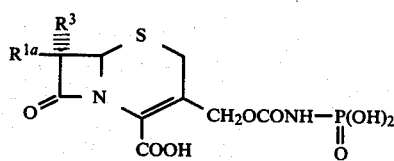

(I')

(wherein $R^{1a}$ represents an acylamido group, conveniently one which contains 1 to 40 e.g. 1 to 25 carbon atoms; and $R^3$ is as defined above) and non-toxic derivatives thereof.

We have now discovered a new process for preparing cephalosporin compounds having a phosphonocarbamoyloxymethyl

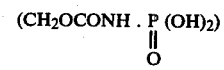

group at the 3-position, for example, of the type described in said Patent Application, which comprises treating a corresponding 3-(disubstituted-phosphoryl)-carbamoyloxymethyl compound with a silyl reagent, followed by hydrolysis to form a 3-phosphonocarbamoyloxymethyl compound. A particular advantage of our new process is that the hydrolysis of the disubstituted phosphoryl group can be effected under very mild conditions which may avoid any undesired removal of other labile groups present in the cephalosporin molecule.

Thus, according to one aspect of the present invention we provide a process for the preparation of cephalosporins have a phosphonocarbamoyloxymethyl group at the 3-position, which comprises reacting a cephalosporin having at the 3-position a group of the formula

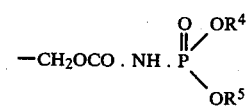

[wherein $R^4$ and $R^5$, which may be the same or different, each represents an alkyl (preferably a lower ($C_{1-3}$) alkyl, e.g. methyl or ethyl), aralkyl, alicyclic or aryl group, or $R^4$ and $R^5$ together form a divalent group with at least 3 carbon atoms bridging the oxygen atoms] with a compound of formula

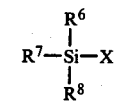

(wherein $R^6$, $R^7$ and $R^8$, which may be the same or different, each represents an alkyl (preferably a lower ($C_{1-3}$) alkyl, e.g. methyl or ethyl), aralkyl, alicyclic or aryl group, or any two of $R^6$, $R^7$ and $R^8$ together form a divalent group containing at least 3 carbon atoms; and X represents a chlorine, bromine or iodine atom) followed by hydrolysis.

According to a preferred embodiment of the present invention we provide a process for the preparation of compounds of the general formula (I) (as hereinbefore defined) and salts thereof which comprises reacting a compound of the formula

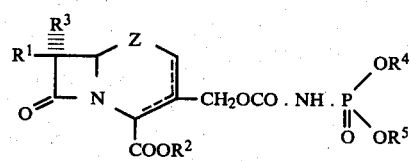

(II)

(wherein $R^1$, $R^2$, $R^3$, $R^4$, $R^5$, Z and the dotted line are as defined above) with a compound of formula

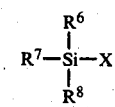

(III)

(wherein $R^6$, $R^7$, $R^8$ and X are as defined above) followed by hydrolysis; whereafter, if necessary and/or desired in each instance, any of the following reactions, in any appropriate sequence, are carried out:

(i) conversion of a $\Delta^2$ isomer into a desired $\Delta^3$ isomer,
(ii) reduction of a cephalosporin sulphoxide product to yield the corresponding sulphide,
(iii) conversion of a precursor for a desired acylamido group into that said group, e.g. by removal of a protecting group, and
(iv) removal of any carboxyl blocking group of any hydroxyl or amino protecting groups, and finally recovering the desired compound of formula (I), if necessary after separation of isomers, and if desired, after conversion of the compound to a salt thereof.

The process of the present invention may be used for the preparation of the above-defined compounds of general formula (I') and non-toxic derivatives thereof, which compounds are preferred.

The term 'non-toxic' as applied to the derivatives of the compounds of formula (I') means those derivatives which are physiologically acceptable in the dosages at which they are administered. Such derivatives may include, for example, salts, 1-oxides and solvates e.g. hydrates, of the compound of formula (I'), and, where appropriate combinations thereof.

It should be appreciated that all cephalosporin formulae herein are skeletal formulae and are intended to embrace closely related analogues such as 2-methyl, 2-methylene and 2,2-dimethyl cephalosporins.

The reaction of the cephalosporin compound of formula (II) with the silyl reagent of formula (III) is preferably effected at a temperature in the range from $-50°$ C. to $+100°$ C., advantageously when X in the compound of formula (III) is bromine from $-5°$ C. to $+25°$ C. This reaction is conveniently carried out in an inert solvent medium comprising for example a hydrocarbon (e.g. benzene), chlorinated hydrocarbon (e.g. methylene dichloride), ether (e.g. tetrahydrofuran) or ester (e.g. ethyl acetate). Mixtures of solvents, e.g. comprising two or more of the above-described solvents, may also be used. When the compound of formula (II) contains an acid-sensitive function, such as a syn oxime group which may isomerise to the corresponding anti isomer, the reaction of this compound with the silyl reagent is preferably effected in the presence of a hydrogen halide acceptor which does not cause isomerisation or lactonisation in the cephalosporin ring, for example a base, e.g. pyridine or a basic derivative thereof; or a neutral acid scavenger, e.g. a silyl amide such as N-trimethylsilylacetamide, N-trimethylsilyltrifluoroacetamide or N,N-bis-(trimethylsilyl)acetamide, a silylurethane such as trimethylsilylurethane, or an oxirane such as ethylene oxide or D,L-2-methyloxirane. Trimethylsilylurethane is preferred.

In the above reaction, a molar excess of the compound of formula (III) is preferred. When compounds of formula (II) wherein $R^2$ is a carboxyl blocking group are employed as starting materials 1, to 3 moles of the compound of formula (III) are preferably employed per mole of the said compound of formula (II). When compounds of formula (II) wherein $R^2$ is hydrogen are employed as starting materials, 2 to 6 moles of the compound of formula (III) are preferably employed per mole of the said compound of formula (II). The abovementioned hydrogen halide acceptor is preferably used in an equimolar amount with the compound of formula (III).

A compound of formula (III) wherein X is bromine or iodine for use in the process of the invention may, if desired, be formed in situ by employing a compound of formula (III) wherein X is chlorine together with a bromide or iodide salt of an alkali metal, (e.g. lithium, sodium or potassium).

Examples of the groups $R^4$, $R^5$, $R^6$, $R^7$ and $R^8$ defined above include $C_{1-4}$ alkyl; benzyl or phenethyl, cyclohexyl or cyclopentyl; or phenyl groups.

Preferred compounds of formula (III) for use in the process according to the present invention include those wherein at least one of the $R^6$, $R^7$ and $R^8$ groups is methyl and wherein X is bromine, trimethylsilyl bromide being a particularly preferred compound of formula (III).

Particularly preferred compounds of formula (II) include those wherein at least one of the groups $R^4$ and $R^5$ is methyl or ethyl.

Acylamido groups which may be present at the 7-position of the cephalosporin starting materials and products in the process of the invention [e.g. as the group $R^1$ in compounds of formulae (I), (I') and (II)] may, for example, be selected from the wide range of side chain acylamido groups known in the $\beta$-lactam antibiotic art.

Specific acyl groups which may be present in acylamido groups $R^1$ are illustrated in the following list, which is not intended to be exhaustive:

(i) $R^uC_nH_{2n}CO-$ where $R^u$ is aryl (carbocyclic or heterocyclic), cycloalkyl, substituted aryl, substituted cycloalkyl, cycloalkadienyl, or a non-aromatic or mesionic group, and n is an integer from 1-4. Examples of this group include phenylacetyl wherein the phenyl group may if desired be substituted by, for example, one or more of fluoro, nitro, protected amino, protected hydroxy (e.g. esterified hydroxy such as acetoxy), methoxy, methylthio or methyl; N,N-bis (2-chloroethyl) aminophenylpropionyl; thien-2 and -3-ylacetyl; 3- and 4-isoxazolylacetyl either substituted or unsubstituted; pyridylacetyl; tetrazolylacetyl; cyclohexadienylacetyl; or a sydnoneacetyl group. Where n is other than O, especially where n is 1, the $\alpha$-carbon atom of the acyl group may be substituted by, for example, an esterified hydroxy (e.g. acyloxy such as formyloxy or lower alkanoyloxy), etherified hydroxy (e.g. methoxy), protected amino, carboxy, esterified carboxy, triazolyl, tetrazolyl or cyano group or a halogen atom; examples of such $\alpha$-substituted acyl groups include esterified 2-hydroxy-2-phenylacetyl, N-blocked 2-amino-2-phenylacetyl, 2-carboxy-2-phenylacetyl and esterified 2-carboxyl-2-phenylacetyl.

(ii) $C_nH_{2n+1}CO-$ where n is O or an integer from 1-7. The alkyl group may be straight or branched and, if desired, may be interrupted by an oxygen or sulphur atom and/or may be substituted by, for example, a cyano group, a carboxy or esterified carboxy group (e.g. an alkoxycarbonyl group), an esterified hydroxy group, a blocked amino group or a carboxycarbonyl (—CO.COOH) or esterified carboxycarbonyl group. Examples of such groups include formyl, cyanoacetyl, butylthioacetyl, hexanoyl, heptanoyl, octanoyl, glutaroyl, esterified glutaroyl, and N-blocked (e.g. N-ethoxycarbonyl or N-benzoyl) and optionally esterified R-5-amino5-carboxypentanoyl (e.g. R-5-benzamido-5-diphenylmethoxycarbonylpentanoyl or R-5-diphenylmethoxycarbonyl-5-isobutoxycarbonylaminopentanoyl).

(iii)

where $R^u$ has the meaning defined under (i) and in addition may be benzyl, $R^v$ and $R^w$ (which may be the same or different) each represents hydrogen, phenyl, benzyl, phenethyl or lower alkyl and Y is an oxygen or sulphur atom. Examples of such groups include phenoxyacetyl, 2-phenoxy-2-phenylacetyl, phenoxypropionyl, 2-phenoxybutyryl, benzyloxycarbonyl, 2-phenoxypropionyl, 2-phenoxybutyryl, methylthiophenoxyacetyl, phenylthioacetyl, chloro- and fluoro-phenylthioacetyl, pyridylthioacetyl and benzylthioacetyl.

(iv) Substituted glyoxylyl groups of the formula $R^y$-CO.CO— where $R^y$ is an aliphatic, araliphatic or aromatic group, e.g. phenyl, thienyl or furyl or a fused benzene ring. Also included in this class are the α-carbonyl derivatives of the above substituted glyoxylyl groups, e.g. the α-alkoxyimino, α-aryloxyimino and α-acyloxyimino derivatives, especially those possessing the syn-configuration with respect to the 7-carboxamido group. Groups of this type, of which an example is the Z-2-(fur-2-yl)-2-methoxyiminoacetyl group, include those represented by the formula

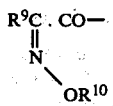

[wherein $R^9$ represents hydrogen or an organic group (especially a carbocyclic or heterocyclic aromatic group such as phenyl, naphthyl, thienyl, thiazolyl e.g. aminothiazolyl, or furyl) and $R^{10}$ represents hydrogen, an acyl group (e.g. a lower alkanoyl, alkenoyl, alkynoyl, haloalkanoyl, alkoxycarbonyl, haloalkoxycarbonyl, alkylthiocarbonyl or aralkyloxycarbonyl group or an aroyl or carbamoyl group) or an etherifying group (e.g. a lower alkyl, alkenyl, alkynyl, cycloalkyl, cycloalkenyl or aralkyl group, carboxylic or heterocyclic aryl group, or any of these groups substituted by a carboxy, esterified carboxy, aminocarbonyl or N-substituted aminocarbonyl group)], as described in greater detail in Belgian Pat. Nos. 778,630, 783,449, 801,997, 806,450, 823,651 and 843,152.

The process according to the present invention is particularly applicable to the preparation of 3-phosphonocarbamoyloxymethyl-7-[Z-2-(fur-2-yl)-2-methoxyiminoacetamido]ceph-3-em-4-carboxylic acid and salts thereof.

As indicated above, compounds of general formula (I) may be readily converted to corresponding 3-carbamoyloxymethyl cephalosporins of formula

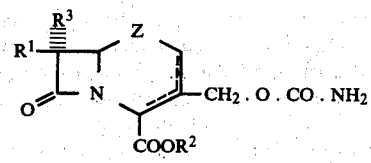
(IV)

(wherein $R^1$, $R^2$, $R^3$, Z and the dotted line have the above defined meanings). This conversion may be effected by hydrolysis as described in U.K. Patent Application No. 7,912,215.

The starting materials of formula (II) employed in the process of the present invention may advantageously be prepared by reacting a corresponding 3-hydroxymethyl cephalosporin compound of formula

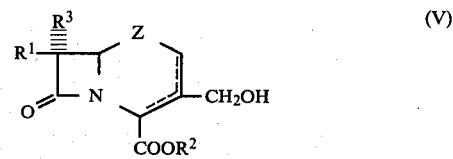
(V)

(wherein $R^1$, $R^2$, $R^3$, Z and the dotted line are as defined above) with a P-substituted phosphinyl isocyanate of formula

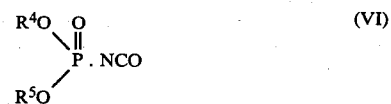
(VI)

(wherein $R^4$ and $R^5$ are as defined above), this process constituting a further feature of the invention.

In the preparation of compounds of general formula (II) by the process, it is convenient to employ substantially equimolar amounts of the 3-hydroxymethyl cephalosporin and the P-substituted phosphinyl isocyanate (VI); the use of a small excess (e.g. up to 0.5 moles) of the compound (VI) may, however, be advantageous e.g. to allow for side reactions between this reagent and hydroxylic impurities (e.g. water) in the reaction system. In view of the susceptibility of P-substituted phosphinyl isocyanates to reaction with water, the reaction with the 3-hydroxymethyl cephalosporin is desirably conducted under anhydrous conditions; thus, for example, the reactions may be carried out under an appropriate desiccant or the reaction system may be kept dry by passage of a stream of an anhydrous inert gas such as nitrogen.

The temperature employed in the reaction of the 3-hydroxymethyl cephalosporin and P-substituted phosphinyl isocyanate may, for example, be in the range $-50°$ to $+105°$ C., e.g. $-20°$ to $+50°$ C.; the reaction may conveniently be carried out at room temperature (e.g. $+15°$ to $+30°$ C.). The reaction is exothermic, so that cooling of the reaction system may be desirable in order to maintain a steady temperature.

The reaction of the 3-hydroxymethyl cephalosporin compound with the P-substituted phosphinyl isocyanate is conveniently carried out in solution, for example in an inert organic solvent, since this facilitates control of reaction conditions such as temperature. Solvents which may be used include chlorinated hydrocarbons such as methylene chloride or 1,2-dichloroethane; ethers such as tetrahydrofuran, dioxan or diethylene glycol dimethyl ether (diglyme); esters such as ethyl acetate; ketones such as acetone; hydrocarbons such as benzene or cyclohexane and nitriles such as acetonitrile. Mixtures of solvents, e.g. comprising two or more of the above-described solvents, may also be used. As indicated above, the solvent should desirably be substantially free from hydroxylic impurities to avoid unwanted side reactions involving the P-substituted phosphinyl isocyanate.

Any blocking group substituting the 4-carboxy group of the compounds of formulae (I), (II), (IV) and (V) is desirably a group which may readily be split off at a later stage of a reaction sequence and advantageously is a group containing 1–20 carbon atoms. Suitable blocked carboxyl groups are well known in the art, a list of representative groups being included in our Belgian Pat. No. 783,449. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may, if desired, be subsequently removed by any of the appropriate methods disclosed in the literature. It will of course be appreciated that $R^2$ may represent an ester group in a compound which is to be used in medicine in which case this group should be physiologically acceptable. When such an ester group is employed it may not be necessary or desirable to effect deprotection of the carboxyl group.

It will be appreciated that where the acylamido group at the 7-position carries substituents such as amino, hydroxy or mercapto groups, which are susceptible to reaction with P-substituted phosphinyl isocyanates, these substituents should be protected by substitution with an appropriate group unless further reaction is desired in a particular instance. Thus, for example, amino groups may be protected by substitution with a mono- or divalent blocking group, suitable groups including acyl groups, for example lower alkanoyl such as acetyl, substituted lower alkanoyl, e.g. lower haloalkanoyl or phenylacetyl and aroyl such as benzoyl or phthaloyl; lower alkoxycarbonyl groups such as ethoxycarbonyl, isobutyloxycarbonyl or t-butoxycarbonyl and substituted lower alkoxycarbonyl groups e.g. lower haloalkoxycarbonyl such as 2,2,2-trichloroethoxycarbonyl; aryl-lower alkoxycarbonyl groups such as benzyloxycarbonyl; sulphonyl groups, for example lower alkylsulphonyl such as methanesulphonyl and arylsulphonyl such as benzene sulphonyl or p-toluene sulphonyl; ylidine groups formed by reaction with an aldehyde or ketone which forms a Schiff's base, for example acetone, methylethylketone, benzaldehyde, salicylaldehyde or ethyl acetoacetate; and divalent groups such that the nitrogen atom forms part of a dihydropyridine ring (protecting groups of this last sort being obtained by, for example, reaction with formaldehyde and a β-ketoester, e.g. acetoacetic ester, as described in our Belgian Pat. No. 771,694). Hydroxyl and mercapto groups may for example, be protected by substitution with carboxylic or sulphonic acyl groups in like manner to amino groups, or, where appropriate, by etherification or thioetherification (e.g. to introduce a branched lower alkyl group such as isopropyl or t-butyl or an aralkyl group such as benzyl, benzyl substituted by one or more methoxy groups, diphenylmethyl or triphenylmethyl). The protecting groups may subsequently be removed from the cephalosporin product by methods well known in the art, for example by hydrolytic, reductive or acid-induced cleavage as appropriate.

Where the acylamido group is substituted by a carboxyl group it may also be advantageous to protect this during the course of the reaction, for example by esterification to introduce an ester group as herein described in connection with the group $R^2$.

3-Dimethoxyphosphorylcarbamoyloxymethyl-7-[Z-2-(fur-2-yl)-2-methoxyiminoacetamido]ceph-3-em-4-carboxylic acid which may be employed as a starting material of formula (II) is a novel compound and constitutes a further feature of the present invention.

If desired, the starting materials of formula (II) wherein $R^1$ represents an amino group may be prepared from corresponding compounds of formula (II) wherein $R^1$ represents an acylamido group, e.g. using the technique described in British Patent Specification No. 1,041,985, the latter compounds of formula (II) being prepared from the corresponding 3-hydroxymethyl compounds, as described above.

Where at the end of a given preparative sequence the sulphoxide analogue of the compound of formula I is obtained, conversion to the corresponding sulphide may, for example, be effected by reduction of the corresponding acyloxysulphonium or alkyloxysulphonium salt prepared in situ by, for example, reaction with acetyl chloride in the case of an acetoxysulphonium salt, reduction being effected by, for example, sodium dithionite or by iodide ion (as in a solution of potassium iodide in a water miscible solvent such as acetic acid, tetrahydrofuran, dioxan, dimethylformamide or dimethylacetamide). The reaction may be effected at a temperature of $-20°$ to $+50°$ C.

Where the reaction product is a ceph-2-em-4-carboxylic ester the desired ceph-3-em compound may be obtained by treatment of the former with a base.

The following Examples illustrate the present invention.

Notes on Experimental

All temperatures are quoted in °C. Melting points were determined in a Mettler apparatus and take the form $(M_y^x)$ where x is the rate of heating (in °C. per minute) and y is the insertion temperature.

Dichloromethane and tetrahydrofuran (THF) were dried by passage through basic alumina, N,N-dimethylformamide (DMF) was dried by passage through acidic alumina and these solvents were stored over molecular sieves.

Structures were confirmed by i.r. and n.m.r. spectra. N.m.r. (nuclear magnetic resonance) spectra were determined at 100 MHz. The integrals were in agreement with the assignments; coupling constants, J, are in Hz, the signs not being determined; s=singlet, d=doublet, dd=double doublet, t=triplet, q=quartet, m=multiplet, and ABq=AB quartet.

T.l.c. is thin-layer chromatography using pre-coated plates (Merck $F_{254}$, 0.25 mm thick coating) which were examined under ultra-violet light at 254 nm and were developed by spraying with ninhydrin in n-butanol and heating to approx. 140° C. or by exposure to iodine vapour.

EXAMPLE 1

(6R,7R)-3-Dimethoxyphosphorylcarbamoyloxymethyl-7-[Z-2-(fur-2-yl)-2-methoxyiminoacetamido]ceph-3-em-4-carboxylic acid A solution of dimethoxyphosphinyl isocyanate (7.25 g), in dry THF (4 ml) was added to a solution of (6R,7R)-7-[Z-2-(fur-2-yl)-2-methoxyiminoacetamido]-3-hydroxymethylceph-3-em-4-carboxylic acid (6.10 g) in dry THF (40 ml) and the resultant mixture was stirred at room temperature for 1.5 hours. The mixture was then evaporated in vacuo to an oily gum which was dissolved in ethyl acetate (50 ml). The resultant organic solution was extracted with saturated aqueous sodium bicarbonate solution (50 ml) and the aqueous extract was washed with ethyl acetate. The aqueous extract was layered with ethyl acetate (30 ml) and was then acidified to pH 0.5 by addition of concentrated hydrochloric acid, and was then extracted with ethyl acetate (3×30 ml) and the combined organic extracts were dried (sodium sulphate) and evaporated in vacuo to a white foam. Trituration of this foam with di-isopropyl ether gave an off-white solid which was redissolved in ethyl acetate. Addition of di-isopropyl ether (400 ml) to the ethyl acetate solution caused precipitation of a solid which after filtration and drying afforded the title compound (8.27 g) as a white solid; m.p. ($M_{50}{}^2$) 72°, $[\alpha]_D{}^{23}+38°$ (c0.96, pH7 phosphate buffer).

EXAMPLE 2

(a)
(6R,7R)-3-Phosphonocarbamoyloxymethyl-7-[Z-2-(fur-2-yl) 2-methoxyiminoacetamido]ceph-3-em-4-carboxylic acid Bromotrimethylsilane (0.61 g), in dichloromethane (3 ml) was added (at 0° under nitrogen) to a stirred solution of (6R,7R)-3-dimethoxyphosphorylcarbamoyloxymethyl-7-[Z-2-(fur-2-yl)-2-methoxyiminoacetamido]-ceph-3-em-4-carboxylic acid (0.53 g) and trimethylsilylurethane (0.965 g) in dry dichloromethane (5 ml). After 1.75 hours no starting cephalosporin remained as indicated by t.l.c.

The mixture was then evaporated in vacuo to an oil which was partitioned between ethyl acetate (25 ml) and saturated aqueous sodium bicarbonate solution (25 ml).

The aqueous phase was then separated and layered with ethyl acetate (20 ml) and acidified to pH 0.5 by addition of concentrated hydrochloric acid.

The acidic aqueous phase was extracted with butan-1-ol (3×20 ml) and the combined extracts were washed with water (10 ml) and then evaporated in vacuo to a white solid which, on trituration with ether gave the title compound (0.475 g) as a white solid, m.p. ($M_{130}{}^2$) 143°, $[\alpha]_D{}^{22}+36.5°$ (c 0.99, pH7 phosphate buffer).

(b)
(6R,7R)-3-Carbamoyloxymethyl-7-[Z-2-(fur-2-yl)-2-methoxyiminoacetamido]ceph-3-em-4-carboxylic acid (cefuroxime)

A solution of (6R,7R)-3-phosphonocarbamoyloxymethyl-7-[Z-2-(fur-2-yl)-2-methoxyiminoacetamido]-ceph-3-em-4-carboxylic acid (0.35 g) in water (4 ml) and dioxan (1 ml) was kept successively at 40° for 5 hours, room temperature for 16 hours, 40° for 6 hours and 20° for 16 hours. The conversion to the title compound was monitored by t.l.c. A precipitate was formed and this was filtered off. The pH was altered from 4 to 7 by addition of saturated aqueous sodium bicarbonate solution.

The resultant mixture was washed with ethyl acetate (25 ml) and the aqueous phase acidified to pH2 (with concentrated hydrochloric acid) which was extracted with ethyl acetate (3×25 ml). The organic extracts were combined and washed successively with water and saturated brine, dried (magnesium sulphate) and evaporated in vacuo to an oil. Trituration of this oil with ether afforded the title compound as a solid (41 mg) with ultraviolet (pH6 phosphate buffer) and n.m.r. (DMSO-d$^6$) spectra in accord with an authentic specimen.

EXAMPLE 3

(6R,7R)-3-Phosphonocarbamoyloxymethyl-7-[Z-2-(fur-2-yl)-2-methoxyiminoacetamido]ceph-3-em-4-carboxylic Acid Bromotrimethylsilane (0.31 g) in dichloromethane (3 ml) was added (at 0°, under nitrogen) to a stirred solution of pyridine (0.24 ml) and (6R,7R)-3-dimethoxyphosphorylcarbamoyloxymethyl-7-[Z-2-(fur-2-yl)-2-methoxyiminoacetamido]ceph-3-em-4-carboxylic acid (0.53 g) in dry dichloromethane (10 ml) at 0°. After 1.5 hours a further portion of bromotrimethylsilane (0.31 g) was added and the reaction mixture was stirred for a further 3 hours. The reaction mixture was evaporated in vacuo to a solid which was partitioned between ethyl acetate (30 ml) and saturated aqueous sodium bicarbonate solution (30 ml). The aqueous phase was separated off and layered with ethyl acetate and acidified to pH 0.5 by addition of concentrated hydrochloric acid.

The aqueous phase was extracted with butan-1-ol (3×25 ml) and the combined organic extracts were washed with water (10 ml) and were evaporated in vacuo to give a slurry which, on trituration with ether afforded the title compound (0.26 g) as a pale-yellow solid, m.p. ($M_{130}{}^2$) 143°, $[\alpha]_D{}^{22}+42.4°$ (c 0.1, pH7 phosphate buffer).

EXAMPLE 4

(a) (R and S)-1-Acetoxyethyl (6R,7R)-3-dimethoxyphosphoryl-carba moyloxymethyl-7-[Z-2-(fur-2-yl)-2-methoxyiminoacetamido]ceph-3-em-4-carboxylate and (R and S)-1-acetoxyethyl (4R,6R,7R)-3-dimethoxyphosphorylcarbamoyloxymethyl-7-[Z-2-(fur-2-yl)-2-methoxyiminoacetamido]-ceph-2-em-4-carboxylate Potassium carbonate (0.55 g) was added to a stirred mixture of (6R,7R)-3-dimethoxyphosphorylcarbamoyloxymethyl-7-[Z-2-(fur-2-yl)-2-methoxyiminoacetamido]ceph-3-em-4-carboxylic acid (4.26 g) in DMF (10 ml) at room-temperature.

Stirring was continued for 1.5 hours by which time most of the potassium carbonate had dissolved.

The reaction mixture was then cooled to 0° and a solution of (R,S)-1-acetoxyethyl bromide (1.47 g) in DMF (5 ml) was added. The resultant solution was stirred at 0° for 1 hour and was then partitioned between 2 N-hydrochloric acid (100 ml) and ethyl acetate (100 ml). The aqueous phase was further extracted with ethyl acetate (2×50 ml) and the combined organic extracts were washed successively with 2 N-hydrochloric acid (2×100 ml), water (2×100 ml), saturated aqueous sodium bicarbonate solution (2×100 ml), water (2×100 ml), saturated brine (100 ml) and dried (sodium sulphate) and evaporated in vacuo to a foam. A solution of this foam in ethyl acetate (10 ml) was precipitated from diisopropyl ether to give a mixture of the title esters (2.01 g) as a white solid.

$\nu_{max}$ (Nujol) 3180 to 3150 (2×NH), 1790 ($\beta$-lactam), 1764 (CO$_2$R), and 1680 and 1538 cm$^{-1}$ (CONH). The n.m.r. spectrum (DMSO-d$_6$) indicated an approximate $\Delta^3$:$\Delta^2$-isomer ratio of 3:2.

(b) (R and S)-1-Acetoxyethyl (1S,6R,7R)-3-Dimethoxyphosphorylcarbamoyloxymethyl-7-[Z-2-(fur-2-yl)-2-methoxyiminoacetamido]-ceph-3-em-4-carboxylate, 1-oxide m-Chloroperbenzoic acid (0.944 g) in dichloromethane (10 ml) was added at 0° to a stirred solution of two batches of (R and S)-1-acetoxyethyl (6R,7R)-3-dimethoxyphosphorylcarbamoyloxymethyl-7-[Z-2-(fur-2-yl)-2-methoxyiminoacetamido]ceph-3-em-4-carboxylate and its $\Delta^2$ isomer (ratio ca 3:2) (3.34 g) in dry dichloromethane (20 ml). After 25 minutes reaction was not complete (by t.l.c) so another portion of m-chloroperbenzoic acid (93 mg) was added and the reaction mixture was stirred for a further 10 minutes and evaporated in vacuo to a foam. T.l.c. indicated incomplete oxidation so the foam was re-dissolved in dichloromethane and treated with further m-chloroperbenzoic acid (0.236 g) for 20 minutes by which time reaction was complete. The reaction mixture was then evaporated in vacuo to a foam which was dissolved in ethyl acetate (5 ml) and precipitated from excess di-isopropyl ether to give the title compound (3.033 g) as a pale-yellow solid, m.p. ($M_{130}^2$) 150°, $[\alpha]_D^{22}+67.5°$ (c 0.98, DMSO).

(c) (R and S)-1-Acetoxyethyl (6R,7R)-3-Dimethoxyphosphorylcarbamoyloxymethyl-7-[Z-2-(fur-2-yl)-2-methoxyiminoacetamido]ceph-3-em-4-carboxylate Potassium iodide (2.50 g) and acetyl chloride (0.56 ml) were successively added, at 0°, to a solution of the product of (b) above (2.38 g) in DMF (15 ml).

The reaction mixture was stirred for 70 minutes at 0° and was then partitioned between ethyl acetate (100 ml) and 2 N-hydrochloric acid (100 ml). The aqueous phase was extracted with ethyl acetate (2×50 ml) and the combined organic extracts were successively washed with 2 N-hydrochloric acid (100 ml), aqueous sodium metabisulphite solution (2×100 ml), 2 N-hydrochloric acid (100 ml), water (100 ml), saturated aqueous sodium bicarbonate solution (100 ml), water (100 ml) and saturated brine (100 ml). The organic extract was dried (magnesium sulphate) and evaporated in vacuo to a yellow foam which on precipitation from diisopropyl ether afforded the title ester (1.722 g) as a pale-yellow solid, m.p. ($M_{70}^2$) 101°, $[\alpha]_D^{22.5}+22.4°$ (c 0.89, DMSO).

EXAMPLE 5

(a) (R and S)-1-Acetoxyethyl (6R,7R) 3-phosphonocarbamoyloxymethyl-7-[Z-2-(fur-2-yl)-2-methoxyiminoacetamido]ceph-3-em-4-carboxylate Bromotrimethylsilane (0.31 g) in dichloromethane (3 ml) was added to a cooled (0°) stirred mixture of (R and S)-1-acetoxyethyl (6R,7R)-3-dimethoxyphosphorylcarbamoyloxymethyl-7-[Z-2-(fur-2-yl)-2-methoxyiminoacetamido]ceph-3-em-4-carboxylate (0.62 g) and trimethylsilylurethane (0.16 g) in dry dichloromethane (12 ml) in a nitrogen atmosphere. After 2.5 hours the reaction mixture was evaporated in vacuo to a foam. This foam was dissolved in ethyl acetate (30 ml) although a slight precipitate remained. The filtered organic solution was treated with saturated aqueous sodium bicarbonate solution (30 ml) and the aqueous solution was layered with butan-1-ol (20 ml) and acidified to pH 0.5 by addition of concentrated hydrochloric acid. The aqueous phase was extracted with butan-1-ol (2×15 ml) and the combined organic extracts were evaporated in vacuo to give a solid. Trituration of this solid with di-isopropyl ether afforded the title ester (0.396 g) as a solid; $\nu_{max}$ (Nujol) 3270 (NH), 1788 ($\beta$-lactam), 1734 ($CO_2R$) and 1684 and 1540 cm$^{-1}$ (CONH); $\tau$ (DMSO-d$^6$) 0.18 (d, J 8 Hz, NH), 2.9 to 3.4 (broad m, 2 superimposed q, C$\underline{H}$CH$_3$), 4.14 (m, 7-H, mixture of diastereoisomers), 4.76 (m, 6-H, mixture of diastereoisomers), 7.92 (s, OCOCH$_3$) and 8.52 (d, J 5 Hz, CHC$\underline{H}_3$).

(b) (R and S)-1-Acetoxyethyl (6R,7R)-3-carbamoyloxymethyl-7-[Z-2-(fur-2-yl)-2-methoxyiminoacetamido]ceph-3-em-4-carboxylate A solution of (R and S)-1-acetoxyethyl (6R,7R)-3-phosphonocarbamoyloxymethyl-7-[Z-2-(fur-2-yl)-2-methoxyiminoacetamido]ceph-3-em-4-carboxylate (0.226 g) in tetrahydrofuran (5 ml) and pH4 buffer (20 ml) was kept at pH4 for 3.75 hours at 40°.

The solution was poured into saturated aqueous NaHCO$_3$ (20 ml) and extracted with ethyl acetate (2×20 ml). The organic phase was washed with water (2×20 ml) and saturated brine (20 ml) then dried over magnesium sulphate and evaporated to an oil (0.092 g) which, after precipitation from ethyl acetate-petrol (b.p. 40° to 60°) gave the title ester (0.054 g) as a solid; $[\alpha]_D^{22}+57.3°$ (c 1.08, DMSO) $\nu_{max}$ (CHCl$_3$) 281 nm (E$_{1\ cm}^{1\%}$ 289, $\epsilon$14750).

We claim:

1. In a process for the preparation of a compound of formula

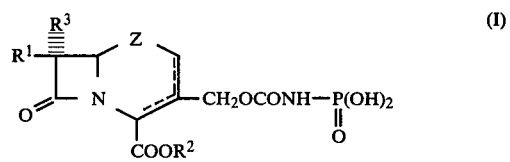

wherein R$^1$ represents a C$_1$-C$_{40}$ protected amino group, R$^2$ represents a group selected from the group consisting of hydrogen atoms and carboxyl blocking groups, R$^3$ represents a group selected from the group consisting of hydrogen atoms and C$_1$-C$_8$ alkyl, C$_1$-C$_8$ alkylthio and C$_1$-C$_8$ alkoxy groups; Z is >S or >S→O ($\alpha$- or $\beta$-); and the dotted line bridging the 2-, 3- and 4-positions of the molecule indicates that the compounds may be ceph-2-em or ceph-3-em compounds, and salts thereof, the steps which consist of reacting a compound of formula

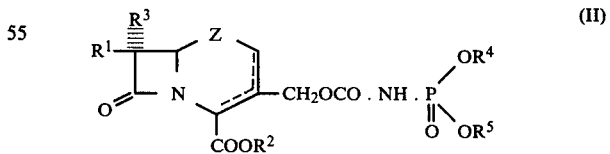

wherein R$^1$, R$^2$, R$^3$, Z and the dotted line are as herein defined, and R$^4$ and R$^5$, which may be the same or different, each represents a group selected from the group consisting of alkyl, aralkyl, alicyclic or aryl groups, or R$^4$ and R$^5$ together form a divalent group with at least 3 carbon atoms bridging the oxygen atoms, with a compound of formula

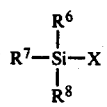

(III)

wherein R$^6$, R$^7$ and R$^8$, which may be the same or different, each represents a group selected from the group consisting of alkyl, aralkyl, alicyclic or aryl groups, or any two of R$^6$, R$^7$ and R$^8$ together form a divalent group containing at least 3 carbon atoms; and X represents an atom selected from the group consisting of chlorine, bromine or iodine atoms, followed by hydrolysis.

2. The process of claim 1 for the preparation of 3-phosphonocarbamoyloxymethyl-7-[Z-2-(fur-2-yl)-2-methoxyiminoacetamido]ceph-3-em-4-carboxylic acid and non-toxic derivatives thereof wherein the reaction is effected in the presence of a hydrogen halide acceptor which does not cause isomerisation or lactonisation in the cephalosporin ring.

3. In a process for the preparation of compounds of formula

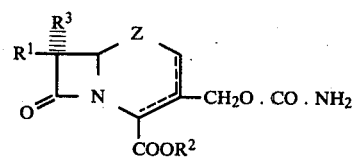

(IV)

wherein R$^1$ represents a C$_1$–C$_{40}$ protected amino group, R$^2$ represents a group selected from the group consisting of hydrogen atoms and carboxyl blocking groups, R$^3$ represents a group selected from the group consisting of hydrogen atoms and C$_1$–C$_8$ alkyl, C$_1$–C$_8$ alkylthio and C$_1$–C$_8$ alkoxy groups; Z is >S or >S→O ($\alpha$- or $\beta$-); and the dotted line bridging the 2-, 3- and 4-positions of the molecule indicates that the compounds may be ceph-2-em or ceph-3-em compounds, and salts thereof, by hydrolysing a compound of formula

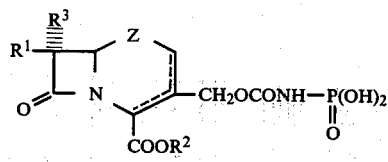

(I)

wherein R$^1$, R$^2$, R$^3$, Z and the dotted line are as herein defined, the improvement which consists of preparing the compound of formula (I) by a process as claimed in claim 1.

* * * * *